United States Patent
Matsumoto et al.

(10) Patent No.: US 12,036,064 B2
(45) Date of Patent: Jul. 16, 2024

(54) BIOLOGICAL SOUND MEASURING DEVICE, METHOD FOR OPERATING BIOLOGICAL SOUND MEASURING DEVICE, AND PROGRAM FOR OPERATING BIOLOGICAL SOUND MEASURING DEVICE

(71) Applicant: OMRON HEALTHCARE CO., LTD., Muko (JP)

(72) Inventors: Naoki Matsumoto, Kyoto (JP); Kenji Hashino, Kyoto (JP); Kei Asai, Kyoto (JP); Naoto Ohgami, Kyoto (JP)

(73) Assignee: OMRON HEALTHCARE CO., LTD., Kyoto (JP)

(*) Notice: Subject to any disclaimer, the term of this patent is extended or adjusted under 35 U.S.C. 154(b) by 959 days.

(21) Appl. No.: 17/060,172

(22) Filed: Oct. 1, 2020

(65) Prior Publication Data
US 2021/0015445 A1   Jan. 21, 2021

Related U.S. Application Data

(63) Continuation of application No. PCT/JP2019/015680, filed on Apr. 10, 2019.

(30) Foreign Application Priority Data

Apr. 18, 2018   (JP) ................. 2018-080190

(51) Int. Cl.
  *A61B 7/04*   (2006.01)
  *A61B 5/02*   (2006.01)
  *A61B 5/0225*   (2006.01)

(52) U.S. Cl.
  CPC .............. *A61B 7/04* (2013.01); *A61B 5/0225* (2013.01)

(58) Field of Classification Search
  CPC ... A61B 5/00; A61B 5/02–021; A61B 5/0225; A61B 7/00–04
  See application file for complete search history.

(56) References Cited

U.S. PATENT DOCUMENTS 9,770,190 B2 *   9/2017   Herscovici-Cohen ....................... A61B 7/003
11,278,258 B2 *   3/2022   Hashino .................. G10L 25/66
(Continued)

FOREIGN PATENT DOCUMENTS

CN   107184231 A   9/2017
JP   2000-060846 A   2/2000
(Continued)

OTHER PUBLICATIONS

Official Communication issued in corresponding Chinese Patent Application No. 201980026018.X mailed on Nov. 3, 2021.
(Continued)

*Primary Examiner* — Nguyen Q. Ha
(74) *Attorney, Agent, or Firm* — Keating & Bennett, LLP

(57) ABSTRACT

There is provided a biological sound measuring device, including: a main body including: a first sound measuring instrument, a housing that has an opening, a second sound measuring instrument, and a controller that causes a sound generator to generate a sound in a state where the opening in the housing is not closed, that determines whether or not a relationship between a measurement sensitivity of the first sound measuring instrument and a measurement sensitivity of the second sound measuring instrument satisfies a condition set in advance, and that when it is determined that the relationship does not satisfy the condition, notifies that it is unable to ensure measurement accuracy of biological sound (Continued)

or adjusts the measurement sensitivity of one or both of the first sound measuring instrument and the second sound measuring instrument.

10 Claims, 10 Drawing Sheets

(56) References Cited

U.S. PATENT DOCUMENTS

| | | |
|---|---|---|
| 2007/0106179 A1 | 5/2007 | Bagha et al. |
| 2011/0034831 A1 | 2/2011 | Christensen et al. |
| 2011/0213274 A1 | 9/2011 | Telfort et al. |
| 2013/0102937 A1 | 4/2013 | Ehrenreich et al. |
| 2013/0345606 A1 | 12/2013 | Ehrenreich et al. |
| 2013/0345608 A1 | 12/2013 | Ehrenreich et al. |
| 2014/0037096 A1 | 2/2014 | Duisters |
| 2014/0180181 A1 | 6/2014 | von Oepen et al. |
| 2014/0228721 A1 | 8/2014 | Ehrenreich et al. |
| 2014/0236057 A1 | 8/2014 | Ehrenreich et al. |
| 2014/0288472 A1 | 9/2014 | Ehrenreich et al. |
| 2015/0099998 A1 | 4/2015 | Christensen et al. |
| 2015/0141880 A1 | 5/2015 | Ehrenreich |
| 2015/0190307 A1 | 7/2015 | Ehrenreich et al. |
| 2015/0262591 A1 | 9/2015 | Hill |
| 2016/0015359 A1 | 1/2016 | Emmanouilidou et al. |
| 2016/0100817 A1 | 4/2016 | Hussain |
| 2017/0340306 A1 | 11/2017 | Spiegel et al. |
| 2017/0347177 A1 | 11/2017 | Masaki et al. |
| 2018/0177482 A1 | 6/2018 | Hashino et al. |
| 2020/0015774 A1 | 1/2020 | Hussain |
| 2020/0107801 A1 | 4/2020 | Hussain et al. |
| 2020/0107802 A1 | 4/2020 | Hussain et al. |
| 2020/0107803 A1 | 4/2020 | Hussain et al. |
| 2020/0107804 A1 | 4/2020 | Hussain et al. |
| 2020/0107805 A1 | 4/2020 | Hussain et al. |
| 2020/0107806 A1 | 4/2020 | Hussain |
| 2020/0107807 A1 | 4/2020 | Hussain |
| 2020/0107808 A1 | 4/2020 | Hussain |
| 2020/0107809 A1 | 4/2020 | Hussain |
| 2020/0107810 A1 | 4/2020 | Hussain |
| 2020/0113536 A1 | 4/2020 | Hussain |
| 2020/0113537 A1 | 4/2020 | Hussain |
| 2020/0113538 A1 | 4/2020 | Hussain |
| 2020/0113539 A1 | 4/2020 | Hussain |

FOREIGN PATENT DOCUMENTS

| | | |
|---|---|---|
| JP | 2000-060847 A | 2/2000 |
| JP | 2005-160644 A | 6/2005 |
| JP | 2011-505997 A | 3/2011 |
| JP | 2013-508029 A | 3/2013 |
| JP | 2013-219444 A | 10/2013 |
| JP | 2014-117572 A | 6/2014 |
| JP | 2015-504321 A | 2/2015 |
| JP | 2016-054455 A | 4/2016 |
| JP | 2017-536867 A | 12/2017 |

OTHER PUBLICATIONS

Official Communication issued in International Patent Application No. PCT/JP2019/0105680, mailed on Jul. 2, 2019.

Official Communication issued in corresponding Japanese Patent Application No. 2018-080190, mailed on May 10, 2022.

* cited by examiner

BIOLOGICAL SOUND MEASURING DEVICE, METHOD FOR OPERATING BIOLOGICAL SOUND MEASURING DEVICE, AND PROGRAM FOR OPERATING BIOLOGICAL SOUND MEASURING DEVICE

CROSS-REFERENCE TO RELATED APPLICATIONS

This application is a continuation of PCT application No. PCT/JP2019/015680, which was filed on Apr. 10, 2019 based on Japanese Patent Application No. 2018-080190 filed on Apr. 18, 2018, the contents of which are incorporated herein by way of reference.

BACKGROUND

The present invention relates to a biological sound measuring device that is to be brought into contact with a body surface of a living body so as to be used, a method for operating the same, and a program for operating the same.

There has been known a device that uses a microphone to extract, as an electrical signal, a biological sound such as a respiratory sound as a sound of an airflow for ventilating the airway and the alveoli, an adventitious sound that is an abnormal sound during breathing which is generated in pathological conditions such as wheezing or pleural friction, or a cardiac sound (see, for example, Patent Literature 1).

Patent Literature 1 discloses an adhesive patch for measuring an acoustic signal from a human body. The adhesive patch includes a first microphone for recording an acoustic signal from the body, and a second microphone for recording an ambient noise signal, and removes noise of a signal detected by the first microphone based on a detection signal of the second microphone.

As disclosed in Patent Literature 1, in a case where two microphones are used for removing noise of an acoustic signal from the body, sensitivity of the two microphones is necessary to be maintained at a state of the time when the two microphones are manufactured.

Patent Literatures 2 and 3 disclose a sensitivity adjustment method for each microphone in an electronic device equipped with a plurality of microphones. In the sensitivity adjustment method, a sound generated from a speaker is measured by a plurality of microphones, and sensitivity of the plurality of microphones is adjusted based on a measurement result.

Patent Literature 1: JP-A-2011-505997
Patent Literature 2: JP-A-2016-054455
Patent Literature 3: JP-A-2013-219444

In a case where a plurality of microphones are used to improve measurement accuracy of a biological sound as disclosed in Patent Literature 1, it is necessary that a sensitivity ratio or a sensitivity difference of the plurality of microphones be maintained at a value set in advance. However, it is assumed that the sensitivity ratio or the sensitivity difference of the plurality of microphones deviates from a value at the time when the microphones are manufactured due to a usage environment, secular change, or the like of the device.

Therefore, it is effective to add an inspection function to a biological sound measuring device having a plurality of microphones so that it can be checked whether or not the sensitivity ratio or the sensitivity difference of the plurality of microphones is a desired value.

For example, as disclosed in Patent Literatures 2 and 3, a speaker that generates a test sound is provided in a device, and the sensitivity ratio or the sensitivity difference can be determined based on an intensity of the test sound measured by each of the plurality of microphones.

In a biological sound measuring device that measures a biological sound in a state of being in contact with a body surface of a living body, a sound measuring instrument for biological sound measurement is disposed in a space sealed by the body surface of the living body, and a sound measuring instrument for measuring an ambient sound is disposed outside the space, at a portion not sealed by the body surface.

In a case where the above-described inspection function is added to such a biological sound measuring device, it is required that the space, in which the sound measuring instrument for biological sound measurement is disposed, is in a state of not being sealed in order to allow the plurality of sound measuring instruments to measure the test sound under the same condition.

Patent Literatures 2 and 3 disclose that sensitivity adjustment of the plurality of microphones is performed. However, the plurality of microphones is not used for measuring biological sounds, and there is no recognition of the problems described above.

SUMMARY

The present invention has been made in view of the above circumstances, and an object thereof is to provide a biological sound measuring device, a method for operating the biological sound measuring device, and a program for operating the biological sound measuring device capable of preventing a decrease in measurement accuracy in a case of measuring a biological sound by using a plurality of sound measuring instruments.

According to one aspect of the present invention, there is provided a biological sound measuring device, including: a main body including: a first sound measuring instrument that is configured to measure a biological sound, a housing that accommodates the first sound measuring instrument therein, and that has an opening which is closed by a body surface of a living body in a state where the housing is pressed against the body surface, a second sound measuring instrument that is provided outside the housing and that configured to measure an ambient sound of the housing, and a controller that causes a sound generator to generate a sound in a state where the opening in the housing is not closed, that determines whether or not a relationship between a measurement sensitivity of the first sound measuring instrument and a measurement sensitivity of the second sound measuring instrument satisfies a condition set in advance, based on an intensity of the sound measured by the first sound measuring instrument and an intensity of the sound measured by the second sound measuring instrument, and that when it is determined that the relationship does not satisfy the condition, notifies that it is unable to ensure measurement accuracy of biological sound or adjusts the measurement sensitivity of one or both of the first sound measuring instrument and the second sound measuring instrument.

According to other aspect of the present invention, the biological sound measuring device further includes: a cover member that covers the housing and the second sound measuring instrument in the state where the opening in the housing is not closed, and that is detachable with respect to the main body. The sound generator is disposed at a position that is covered by the cover member in a state where the cover member is attached to the main body. When attachment of the cover member is detected by the controller, the controller determines that it is the state where the opening in the housing is not closed.

According to other aspect of the present invention, the cover member is made of a material that prevents transmission of a sound that the first sound measuring instrument and the second sound measuring instrument can measure.

According to other aspect of the present invention, when an intensity of a sound from outside measured by the first sound measuring instrument or the second sound measuring instrument is equal to or less than a first threshold set in advance, the controller detects that the cover member is attached.

According to other aspect of the present invention, the sound generator is provided in the cover member.

According to other aspect of the present invention, the main body further includes the sound generator.

According to other aspect of the present invention, when an intensity of a peripheral sound measured by the first sound measuring instrument or the second sound measuring instrument is equal to or less than a second threshold set in advance and it is the state where the opening in the housing is not closed, the controller causes the sound generator to generate the sound.

According to other aspect of the present invention, there is provided a method for operating a biological sound measuring device including a first sound measuring instrument that is configured to measure a biological sound, a housing that accommodates the first sound measuring instrument therein and that has an opening which is closed by a body surface of a living body in a state where the housing is pressed against the body surface, and a second sound measuring instrument that is provided outside the housing and that is configured to measure an ambient sound of the housing. The method includes: a step of causing a sound generator to generate a sound in a state where the opening in the housing is not closed, determining whether or not a relationship between a measurement sensitivity of the first sound measuring instrument and a measurement sensitivity of the second sound measuring instrument satisfies a condition set in advance, based on an intensity of the sound measured by the first sound measuring instrument and an intensity of the sound measured by the second sound measuring instrument, and when it is determined that the relationship does not satisfy the condition, notifying that it is unable to ensure measurement accuracy of biological sound or adjusting the measurement sensitivity of one or both of the first sound measuring instrument and the second sound measuring instrument.

According to other aspect of the present invention, there is provided a storage medium which stores a program for operating a biological sound measuring device including a first sound measuring instrument that is configured to measure a biological sound, a housing that accommodates the first sound measuring instrument therein and that has an opening which is closed by a body surface of a living body in a state where the housing is pressed against the body surface, and a second sound measuring instrument that is provided outside the housing and that is configured to measure an ambient sound of the housing. The program causes a computer to perform a step of: causing a sound generator to generate a sound in a state where the opening in the housing is not closed, determining whether or not a relationship between a measurement sensitivity of the first sound measuring instrument and a measurement sensitivity of the second sound measuring instrument satisfies a condition set in advance, based on an intensity of the sound measured by the first sound measuring instrument and an intensity of the sound measured by the second sound measuring instrument, and when it is determined that the relationship does not satisfy the condition, notifying that it is unable to ensure measurement accuracy of biological sound or adjusting the measurement sensitivity of one or both of the first sound measuring instrument and the second sound measuring instrument.

Figure 1:
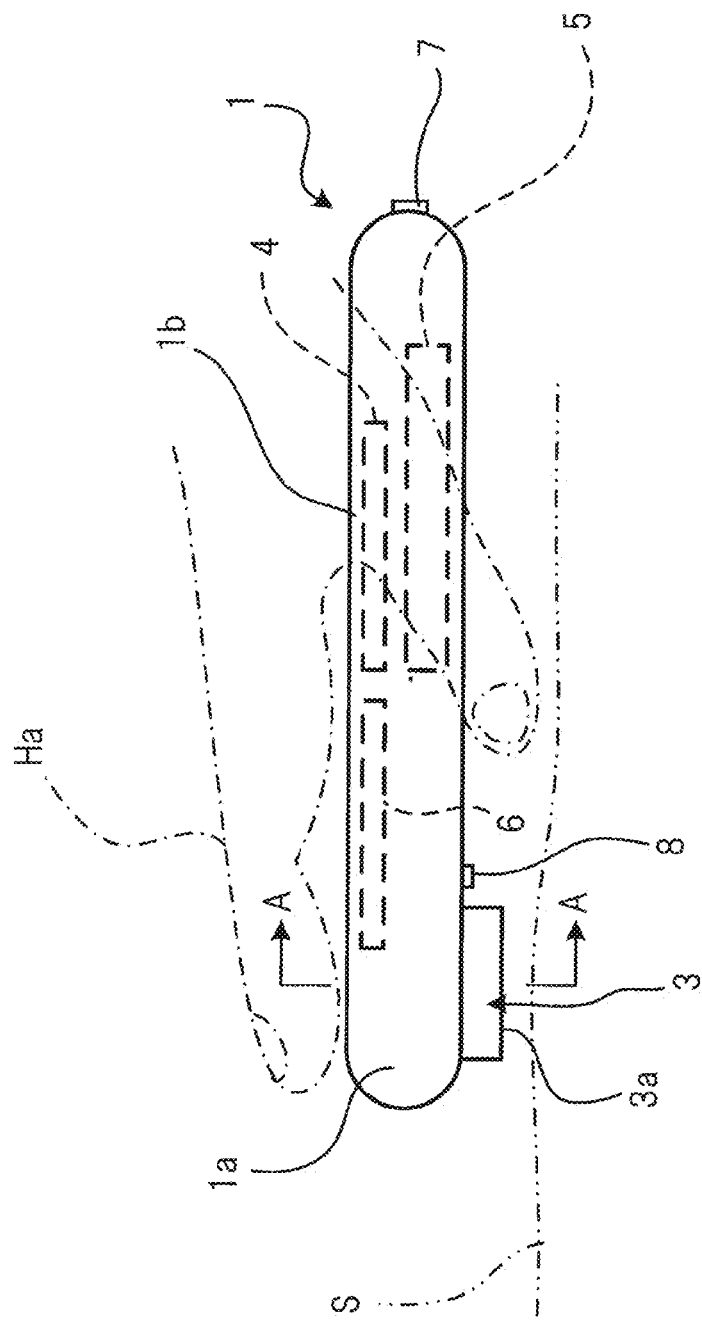
FIG. 1 is a side view illustrating a schematic configuration example of a main body 1 of a biological sound measuring device 100.

DESCRIPTION OF EMBODIMENTS (Outline of Biological Sound Measuring Device of Embodiment)

First, an outline of an embodiment of a biological sound measuring device of the present invention will be described. The biological sound measuring device of the embodiment measures a pulmonary sound (a respiratory sound and adventitious sound) as an example of a biological sound from a human living body, and when it is determined that wheezing is included in a measured sound, the biological sound measuring device reports that. In this way, support is given in determination of whether to give medicine to the subject, determination of whether to bring the subject to a hospital, or diagnosis by a doctor for the subject.

The biological sound measuring device according to the embodiment includes a main body including a first sound measuring instrument for measuring a pulmonary sound, a second sound measuring instrument for measuring an ambient sound, and a sound generator for generating a test sound. The biological sound measuring device measures a pulmonary sound of a living body by using the first sound measuring instrument by sealing a space in which the first sound measuring instrument is accommodated with a body surface. The second sound measuring instrument is used, for example, to remove noise included in the sound to be measured by the first sound measuring instrument other than the pulmonary sound.

In the main body of the biological sound measuring device according to the embodiment, a test sound is generated by the sound generator in a state where the space in which the first sound measuring instrument is disposed is not sealed by the body surface. Further, based on an intensity of the test sound measured by the first sound measuring instrument and an intensity of the test sound measured by the second sound measuring instrument, it is determined whether or not a relationship between a measurement sensitivity of the first sound measuring instrument and a measurement sensitivity of the second sound measuring instrument satisfies a condition set in advance, and when it is determined that the relationship does not satisfy the condition, notification is performed or adjustment of the measurement sensitivity of one or both of the first sound measuring instrument and the second sound measuring instrument is performed.

As contents of the notification, for example, the notification that wheezing cannot be detected, and the notification for prohibiting measurement of biological sound and prompting to repair the device are exemplified. Further, the adjustment of the measurement sensitivity of one or both of the first sound measuring instrument and the second sound measuring instrument is performed so that the above condition is satisfied.

With this processing, even when a measurement sensitivity ratio or a measurement sensitivity difference between the first sound measuring instrument and the second sound measuring instrument is deviated from a value at the time when the sound measuring instruments are manufactured, the measurement sensitivity ratio or the measurement sensitivity difference is corrected or the measurement of a pulmonary sound is prohibited. Therefore, it is possible to prevent the measurement of the pulmonary sound from being performed in a state where the measurement sensitivity ratio or the measurement sensitivity difference is deviated from a desired value, and it is possible to prevent a decrease in measurement accuracy of the pulmonary sound.

Hereinafter, a specific configuration example of the biological sound measuring device of the embodiment will be described.

Embodiment

Figure 4:
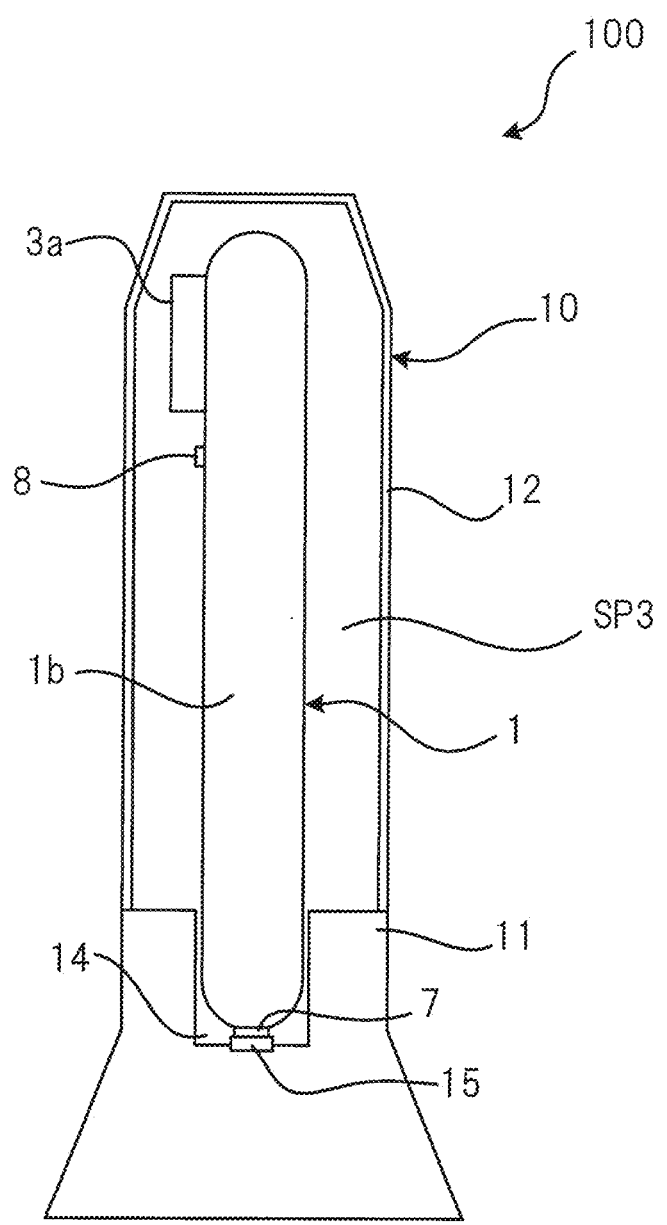
FIG. 4 is a schematic cross-sectional view of the accommodation case 10 in a state where the main body 1 is accommodated.

As illustrated in FIG. 4, a biological sound measuring device 100 according to an embodiment of the biological sound measuring device of the present invention described below includes a main body 1 and an accommodation case 10 for accommodating the main body 1.

FIG. 1 is a side view illustrating a schematic configuration example of the main body 1 of the biological sound measuring device 100. As illustrated in FIG. 1, the main body 1 has a rod-like grip portion 1b formed of a housing made of resin, metal, or the like, and on one end side of the grip portion 1b, a head portion 1a is provided.

Inside the grip portion 1b, a controller 4 that performs overall control of the entire biological sound measuring device 100, a battery 5 that supplies a voltage necessary for operation, and a display unit 6 that displays an image by a liquid crystal display panel, an organic electro luminescence (EL) display panel, or the like are provided. On the other end side of the grip portion 1b, a terminal block 7 for electrically connecting to an accommodation case 10 described later is provided.

The controller 4 includes a central processing unit (CPU), a random access memory (RAM), a read only memory (ROM), and the like, and controls hardware of the biological sound measuring device 100 in accordance with a program. Programs including a program for operating the biological sound measuring device are stored in the ROM of the controller 4.

The head portion 1a is provided with a measuring unit 3 protruding toward one side (a lower side in FIG. 1) in a direction substantially orthogonal to a longitudinal direction of the grip portion 1b, and a sound generator 8. At a tip end of the measuring unit 3, a pressure receiving portion 3a that is to be brought into contact with a body surface S of a living body which is a subject, to receive a pressure from the body surface S, is provided.

In using the main body 1, a user places, for example, an index finger of his/her hand Ha on a back surface of the measuring unit 3 in the head portion 1a, and presses the pressure receiving portion 3a of the measuring unit 3 against the body surface S with the index finger.

Figure 2:
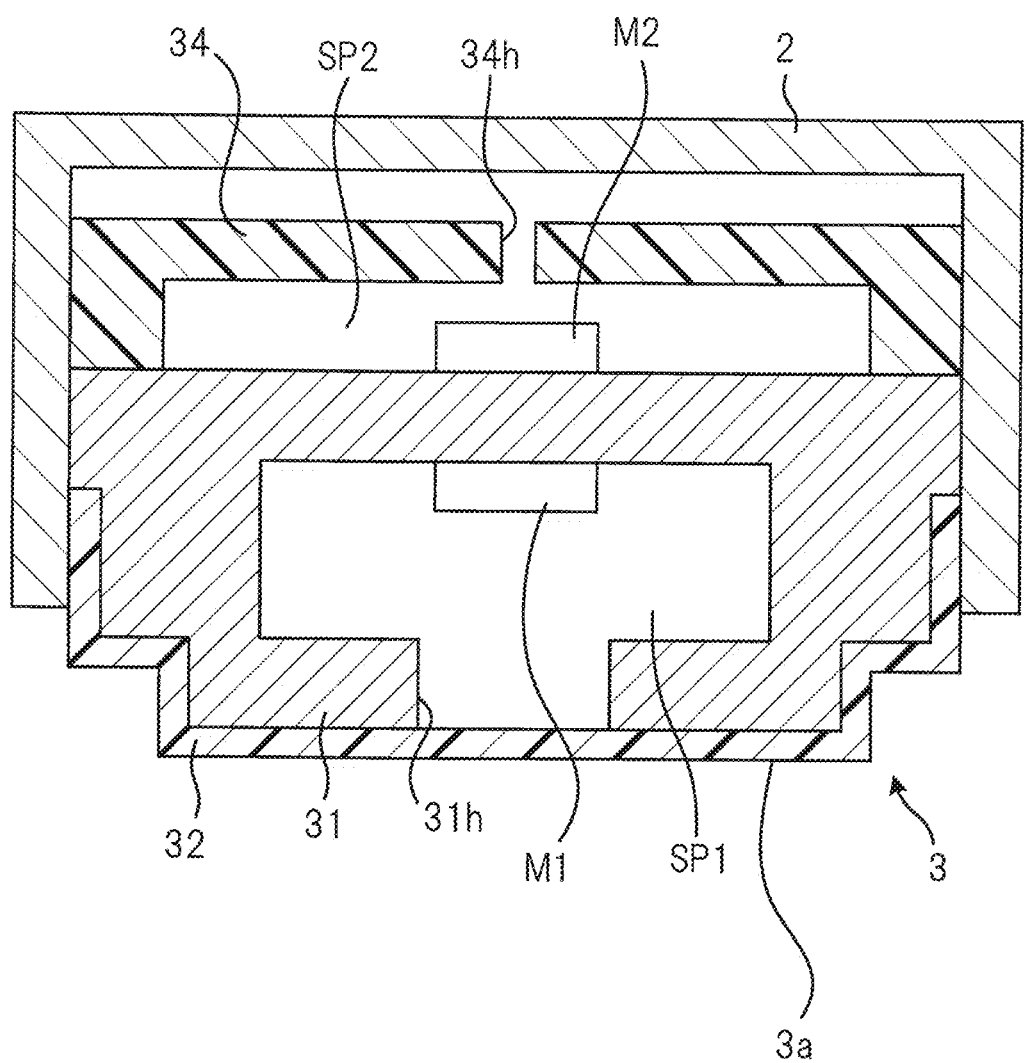
FIG. 2 is a schematic cross-sectional view of the main body 1 taken along a line A-A in FIG. 1.

FIG. 2 is a schematic cross-sectional view of the main body 1 taken along a line A-A in FIG. 1.

As illustrated in FIG. 2, the measuring unit 3 includes: a first sound measuring instrument M1 that measures a sound; a bottomed cylindrical first housing 31 which accommodates the first sound measuring instrument M1 in an accommodation space SP1 therein and which has an opening 31h that is closed by a body surface S of a living body in a state where the housing is pressed against the body surface S; a housing cover 32 that closes the opening 31h from an outer side of the first housing 31 and that covers the first housing 31; a second sound measuring instrument M2 that measures a sound; and a second housing 34 that forms an accommodation space SP2 for accommodating the second sound measuring instrument M2 and that has an opening 34h.

The measuring unit 3 is fitted into an opening portion formed in a housing 2 constituting the head portion 1a, with a part of the housing cover 32 being exposed, and is fixed to the housing 2.

A tip end portion of the part of the housing cover 32, which is exposed from the housing 2, is a flat surface or a curved surface, and this flat surface or curved surface constitutes the pressure receiving portion 3a. The housing 2 is made of resin or the like capable of transmitting a sound.

The first sound measuring instrument M1 is configured to measure a pulmonary sound as a biological sound, and is configured with, for example, a micro electro mechanical systems (MEMS) microphone or a capacitance-type microphone that measures a sound in a frequency band (for example, a frequency range of 10 Hz or more and 10 kHz or less) wider than a frequency range of pulmonary sound (generally, 10 Hz or more and 1 kHz or less).

The first sound measuring instrument M1 is electrically connected to the controller 4 illustrated in FIG. 1 by a lead wire or the like (not illustrated), and transmits information on a measured sound to the controller 4.

At the time of using the main body 1, a state is established where the pressure receiving portion 3a of the housing cover 32 comes into contact with the body surface S and the accommodation space SP1 is sealed by the body surface S via the housing cover 32 under a pressure from the body surface S (hereinafter, this state is referred to as a sealed state).

Further, when the pressure receiving portion 3a vibrates due to the pulmonary sound transmitted from the living body to the body surface S, an internal pressure of the accommodation space SP1 fluctuates due to this vibration, and an electrical signal corresponding to the pulmonary sound is measured by the first sound measuring instrument M1 based on the fluctuation of the internal pressure.

The first housing 31 has a substantially convex shape directed in a lower direction in FIG. 2, and is made of a material having higher acoustic impedance than air and having higher rigidity, such as a resin or a metal. The first housing 31 is made of a material that reflects a sound in a measurement frequency band of the first sound measuring instrument M1 so that the sound is not transmitted from the outside into the accommodation space SP1 in the sealed state.

The housing cover 32 is a bottomed cylindrical member, and a shape of a hollow portion thereof substantially coincides with a shape of an outer wall of the first housing 31.

The housing cover 32 is made of a material having acoustic impedance close to that of a human body, air, or water, and having good flexibility and good biocompatibility. As a material of the housing cover 32, for example, silicon, an elastomer, or the like is used.

The second sound measuring instrument M2 is configured to measure an ambient sound of the first housing 31 (an environmental sound such as human speech, or a sound generated due to rubbing between the main body 1 and the living body or clothing), and is configured with, for example, an MEMS microphone or a capacitance-type microphone that measures a sound in a band (for example, a frequency range of 10 Hz or more and 10 kHz or less) wider than the frequency range of pulmonary sound.

The second sound measuring instrument M2 is electrically connected to the controller 4 illustrated in FIG. 1 by a lead wire or the like (not illustrated), and transmits information on a measured sound to the controller 4.

The second sound measuring instrument M2 is fixed to a surface of the first housing 31, opposite from the pressure receiving portion 3a. A periphery of the second sound measuring instrument M2 is covered with the second housing 34. The second housing 34 is made of a material (for example, a resin) that allows a sound generated around the main body 1 to easily enter the accommodation space SP2 for accommodating the second sound measuring instrument M2.

The opening 34h is formed in the second housing 34. Therefore, a structure is formed in which the sound generated around the main body 1 easily enters the accommodation space SP2 from the opening 34h.

Although the second sound measuring instrument M2 is provided in the measuring unit 3 in the example of FIG. 2, the installation location is not particularly limited as long as the sound generated around the first housing 31 can be measured. For example, the second sound measuring instrument M2 may be provided at a place of the grip portion 1b, which the user is unlikely to touch during use, other than the head portion 1a.

The sound generator 8 provided in the main body 1 illustrated in FIG. 1 is controlled by the controller 4, and generates a sound, as a test sound, in a frequency band that each of the first sound measuring instrument M1 and the second sound measuring instrument M2 can measure. The sound generator 8 may be any type as long as it can convert an electrical signal into physical vibrations, and various types of speakers, for example, can be used.

Figure 3:
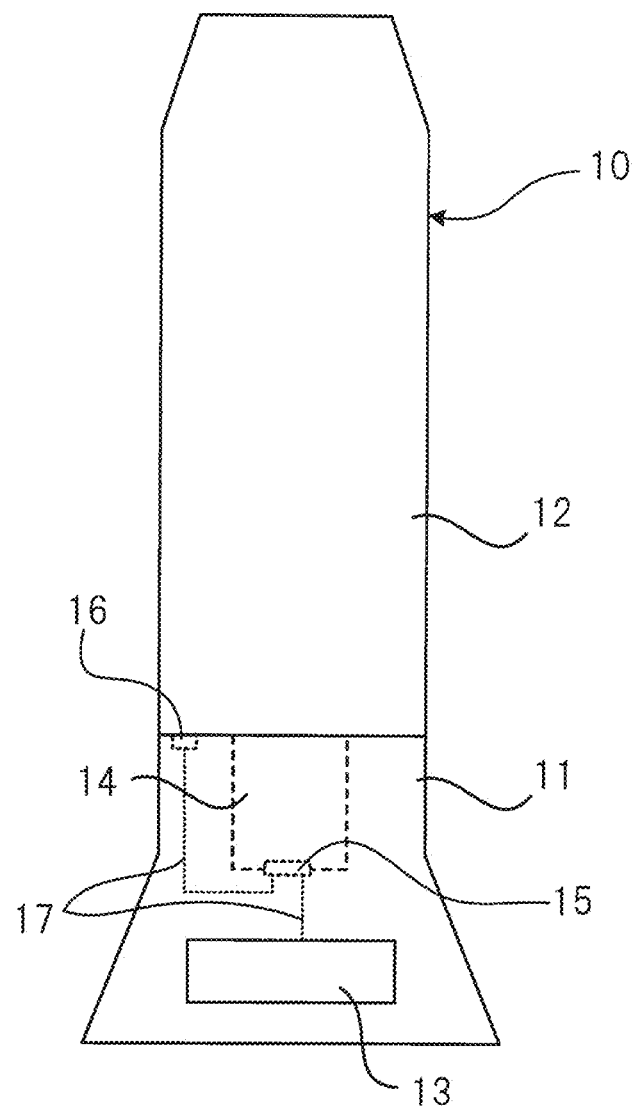
FIG. 3 is a schematic view illustrating a schematic configuration of an accommodation case 10 in which the main body 1 illustrated in FIG. 1 is accommodated.

FIG. 3 is a schematic view illustrating a schematic configuration of the accommodation case 10 in which the main body 1 illustrated in FIG. 1 is accommodated. FIG. 4 is a schematic cross-sectional view of the accommodation case 10 in a state where the main body 1 is accommodated.

The accommodation case 10 includes a base 11 and a bottomed cylindrical lid 12 detachably attached to the base 11.

The base 11 is provided with a display unit 13 that displays an image by a liquid crystal display panel, an organic EL display panel, or the like, a recessed portion 14 that is for supporting the main body 1 with the other end of the grip portion 1b of the main body 1 inserted therein, a terminal block 15 that is provided at a bottom portion of the recessed portion 14, a contact sensor 16 for detecting contact between the base 11 and the lid 12, and a wiring 17.

As illustrated in FIG. 4, the terminal block 15 of the base 11 is electrically connected to the terminal block 7 of the main body 1 in a state where the main body 1 is inserted into the recessed portion 14.

As illustrated in FIG. 3, the terminal block 15 is connected to the display unit 13 and the contact sensor 16 by the wiring 17. Accordingly, in the state where the main body 1 is inserted into the recessed portion 14, an output signal of the contact sensor 16 is transmitted to the controller 4 of the main body 1 via the wiring 17, the terminal block 15, and the terminal block 7. The contact sensor 16 is configured with, for example, a piezoelectric element, and transmits an attachment detection signal to the controller 4 when the lid 12 is attached to the base 11.

In the state where the main body 1 is inserted into the recessed portion 14, the controller 4 of the main body 1 controls the display unit 13 via the terminal block 7, the terminal block 15, and the wiring 17.

As illustrated in FIG. 4, in a state where the main body 1 is inserted into the recessed portion 14 and supported by the base 11, and the lid 12 is attached to the base 11 (in other words, a state where the accommodation case 10 is attached to the main body 1), the main body 1 is disposed in an accommodation space SP3 surrounded by an inner wall of the lid 12 and the base 11.

In this state, as illustrated in FIG. 4, the pressure receiving portion 3a of the measuring unit 3 is not in contact with the inner wall of the lid 12, and the opening 31h in the first housing 31 of the measuring unit 3 is not closed. The sound generator 8 of the main body 1 is disposed at an inner side of the accommodation case 10 (in the accommodation space SP3).

In this manner, in the state where the accommodation case 10 is attached to the main body 1, the accommodation case 10 does not close the opening 31h in the first housing 31 of the main body 1, and covers the first housing 31 and the second sound measuring instrument M2. The accommodation case 10 constitutes a cover member.

Although a material of the base 11 and the lid 12 of the accommodation case 10 is not particularly limited, the material is preferably a material that prevents a sound from entering the accommodation space SP3 from the outside of the accommodation case 10.

For example, the material of the base 11 and the lid 12 of the accommodation case 10 is preferably a material capable of preventing transmission of a sound in a frequency band that each of the first sound measuring instrument M1 and the second sound measuring instrument M2 can measure (reflecting the sound in the frequency band). As such a material, for example, a metal such as SUS, or a rubber such as silicone or urethane can be used.

The main body 1 of the biological sound measuring device 100 has a measurement mode in which a pulmonary sound is measured to determine presence or absence of wheezing (detection of wheezing is performed). In this measurement mode, the controller 4 determines whether or not wheezing is included in the pulmonary sound based on the first sound measured by the first sound measuring instrument M1 and the second sound measured by the second sound measuring instrument M2.

For example, the controller 4 removes noise, other than the pulmonary sound, which is mixed in the first sound measured by the first sound measuring instrument M1, based on the second sound measured by the second sound measuring instrument M2. Further, the controller 4 determines that "wheezing is present" when, for example, the first sound after the noise removal has an intensity equal to or greater than an intensity at which a sound can be determined to be wheezing.

Alternatively, in a case where an intensity of the first sound measured at a certain timing is at a value making the first sound to be considered as wheezing, the controller 4 refers to the second sound measured at the timing, and when an intensity of the second sound is high, determines that influence of an external sound is large and determines that there is no wheezing at the timing.

In order to ensure determination accuracy of the presence or absence of wheezing, a measurement sensitivity SM1 and a measurement sensitivity SM2 are set in advance at the time of manufacturing the biological sound measuring device 100 so that a relationship between the measurement sensitivity SM1 of the first sound measuring instrument M1 and the measurement sensitivity SM2 of the second sound measuring instrument M2 satisfies a condition set in advance. The measurement sensitivity of the sound measuring instrument refers to a ratio of an analog output voltage value or a digital output value of the sound measuring instrument and an input sound pressure.

The relationship is, for example, a ratio of the measurement sensitivity SM1 and the measurement sensitivity SM2, or a difference between the measurement sensitivity SM1 and the measurement sensitivity SM2.

The condition is, for example, that the ratio falls within a range set in advance, or that the difference falls within a range set in advance.

As described above, the measurement sensitivity SM1 of the first sound measuring instrument M1 and the measurement sensitivity SM2 of the second sound measuring instrument M2 may deviate from the values set at the time of manufacturing the biological sound measuring device 100 due to degradation over time or the like.

Therefore, in addition to the measurement mode described above, the main body 1 of the biological sound measuring device 100 has an inspection mode in which the relationship between the measurement sensitivity of the first sound measuring instrument M1 and the measurement sensitivity of the second sound measuring instrument M2 is inspected.

In this inspection mode, the controller 4 determines whether or not the opening 31h in the first housing 31 is in a state of not being closed, and when it is determined to be in this state, causes the sound generator 8 to generate a test sound.

In the biological sound measuring device 100, when the main body 1 is accommodated in the accommodation case 10 (in other words, when the accommodation case 10 is attached to the main body 1), the opening 31h in the first housing 31 is in the state of not being closed. Therefore, when it is detected that the accommodation case 10 is attached to the main body 1, the controller 4 determines that the opening 31h in the first housing 31 is in the state of not being closed, and causes the sound generator 8 to generate a test sound.

When a contact detection signal is received from the contact sensor 16, the controller 4 detects that the accommodation case 10 is attached to the main body 1.

In the inspection mode, after causing the sound generator 8 to generate the test sound, the controller 4 determines whether or not the relationship between the measurement sensitivity SM1 and the measurement sensitivity SM2 satisfies the above condition, based on an intensity m1 of the test sound measured by the first sound measuring instrument M1 and an intensity m2 of the test sound measured by the second sound measuring instrument M2, and performs control corresponding to a determination result.

When it is determined that the relationship does not satisfy the condition, for example, the controller 4 performs control to notify the user that the measurement accuracy of the biological sound cannot be ensured, as the control corresponding to the determination result. For example, the controller 4 performs notification by causing the display unit 13 of the accommodation case 10 to display a message that detection of wheezing is not possible, a message for prohibiting the measurement of pulmonary sound and prompting to repair the device, or the like.

A speaker may be mounted on the accommodation case 10, and the notification may be performed by outputting these messages from the speaker. Alternatively, the main body 1 and an electronic device such as a smartphone may be configured to be able to communicate with each other. A message may be transmitted from the controller 4 to the electronic device, and display or audio output of the message may be performed using a display or a speaker of the electronic device.

Alternatively, for example, a light emitting diode (LED) may be mounted on the accommodation case 10, and when it is determined that the relationship does not satisfy the condition, the controller 4 may notify the user that the measurement accuracy cannot be ensured by causing the LED to emit red light, for example.

When it is determined that the relationship does not satisfy the condition, the controller 4 may perform adjustment of one or both of the measurement sensitivity SM1 and measurement sensitivity SM2 so that the relationship satisfies the condition, as control corresponding to the determination result.

In this case, the controller 4 performs adjustment of the measurement sensitivity SM1 by adjusting gain of an amplifier mounted on the first sound measuring instrument M1, and performs adjustment of the measurement sensitivity SM2 by adjusting gain of an amplifier mounted on the second sound measuring instrument M2.

(Operation Example of Biological Sound Measuring Device 100)

Figure 5:
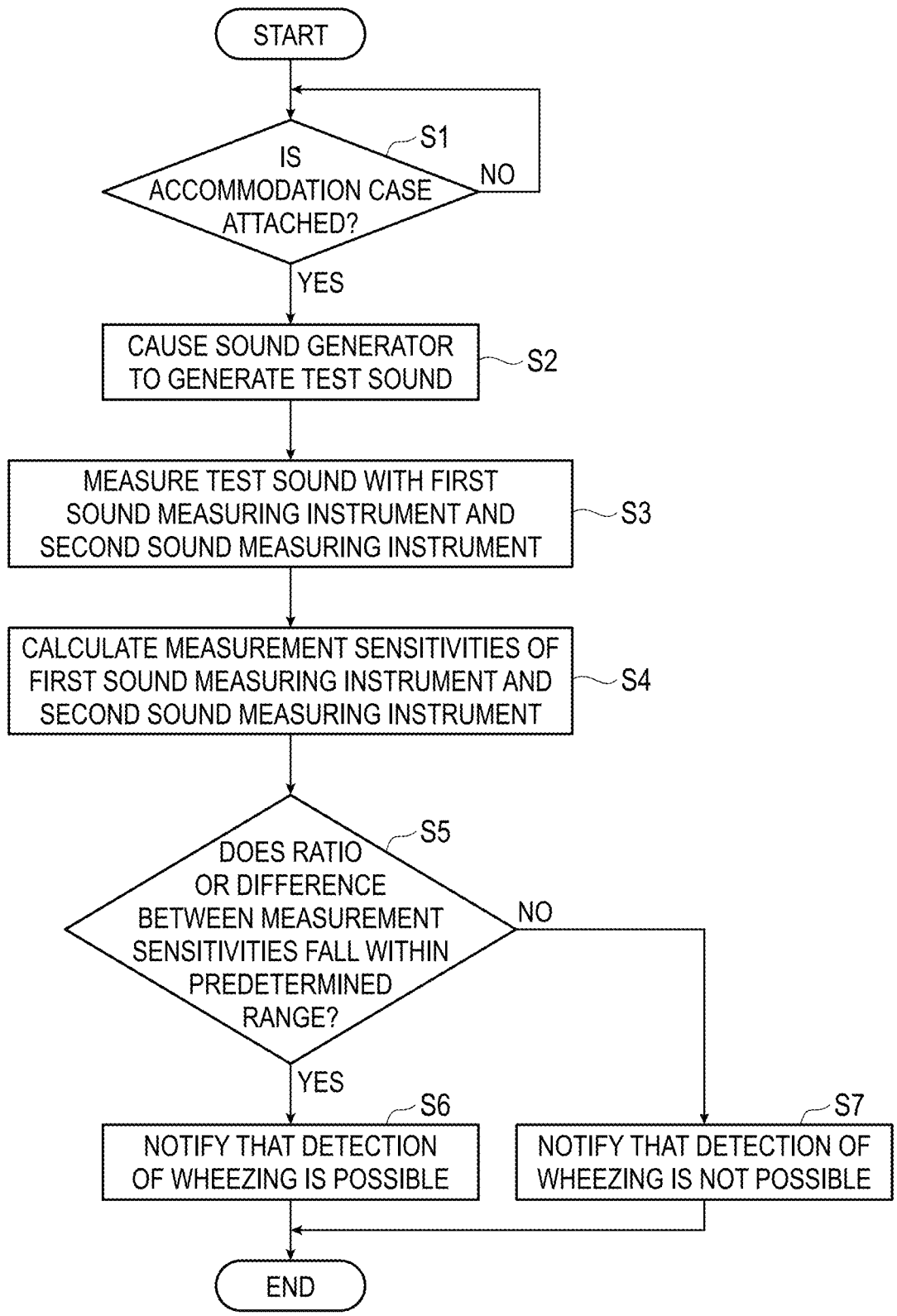
FIG. 5 is a flowchart for illustrating an operation example of the biological sound measuring device 100 in an inspection mode.

FIG. 5 is a flowchart for illustrating an operation example of the biological sound measuring device 100 in an inspection mode.

When the inspection mode is set, the controller 4 determines whether or not the accommodation case 10 is attached to the main body 1 (step S1), and when the accommodation case 10 is attached to the main body 1 (step S1: YES), the controller 4 causes the sound generator 8 to generate a test sound (step S2).

When the accommodation case 10 is not attached to the main body 1, the controller 4 repeats the processing of step S1. When a time period over which it is determined that the accommodation case 10 is not attached to the main body 1 is equal to or longer than a predetermined time period, the controller 4 may cause the display unit 6 of the main body 1 to display a message for prompting to accommodate the main body 1 in the accommodation case 10, and notify the user.

When the test sound is generated in step S2, the test sound is measured by both the first sound measuring instrument M1 and the second sound measuring instrument M2 (step S3).

After the test sound is measured in step S3, the controller 4 acquires an intensity m1 of the test sound measured by the first sound measuring instrument M1 and an intensity m2 of the test sound measured by the second sound measuring instrument M2, calculates the measurement sensitivity SM1 based on the intensity m1 and an intensity of the test sound, and calculates the measurement sensitivity SM2 based on the intensity m2 and the intensity of the test sound (step S4).

Next, the controller 4 obtains a ratio or difference between the measurement sensitivity SM1 and the measurement sensitivity SM2 that are calculated in step S4, and determines whether or not the ratio or difference is within a range set in advance (predetermined range) (step S5).

When the ratio or difference is within the range set in advance (step S5: YES), the controller 4 notifies the user that detection of wheezing is possible, by causing the display unit 13 of the accommodation case 10 to display that (step S6).

When the ratio or difference is outside the range set in advance (step S5: NO), the controller 4 notifies the user that detection of wheezing is not possible, by causing the display unit 13 of the accommodation case 10 to display that (step S7).

As described above, in step S7, the controller 4 may adjust the sensitivity of one or both of the first sound measuring instrument M1 and the second sound measuring instrument M2 so that the relationship between the measurement sensitivity SM1 and the measurement sensitivity SM2 that are calculated in step S4 satisfies the condition, and thereafter perform the processing of step S6.

(Effects of Biological Sound Measuring Device 100)

As described above, according to the biological sound measuring device 100, in the inspection mode, a test sound is generated by the sound generator 8 in a state where the opening 31h in the first housing 31 is not closed. Therefore, the test sound can be measured under substantially the same condition by the first sound measuring instrument M1 and the second sound measuring instrument M2. Accordingly, it is possible to accurately determine whether or not the relationship between the measurement sensitivity of the first sound measuring instrument M1 and the measurement sensitivity of the second sound measuring instrument M2 satisfies the condition.

When this condition is not satisfied, for example, a notification that detection of wheezing is not possible, a notification for prohibiting use of the device and prompting to repair the device, or the like is performed. Therefore, it is possible to prevent the measurement of pulmonary sound from being performed in a state where this condition is not satisfied, and thus it is possible to prevent a decrease in measurement accuracy of pulmonary sound.

Alternatively, when this condition is not satisfied, the measurement sensitivity of the first sound measuring instrument M1 and the measurement sensitivity of the second sound measuring instrument M2 are adjusted so as to satisfy the condition. Therefore, it is possible to prevent the measurement of pulmonary sound from being performed in a state where the condition is not satisfied, and thus it is possible to prevent a decrease in the measurement accuracy of pulmonary sound.

According to the biological sound measuring device 100, when the main body 1 is accommodated in the accommodation case 10, an external sound, other than the test sound generated by the sound generator 8, is less likely to reach the first sound measuring instrument M1 and the second sound measuring instrument M2 that are mounted on the main body 1.

Therefore, it is possible to prevent a sound, other than the test sound generated by the sound generator 8, from entering into the first sound measuring instrument M1 and the second sound measuring instrument M2, and the determination in step S5 of FIG. 5 can be performed with high accuracy.

When the material of the base 11 and the lid 12 of the accommodation case 10 is a material capable of preventing transmission of a sound in a frequency band that each of the first sound measuring instrument M1 and the second sound measuring instrument M2 can measure, the following effects can be obtained.

That is, in a state where the main body 1 is accommodated in the accommodation case 10, the first sound measuring instrument M1 and the second sound measuring instrument M2 mounted on the main body 1 can measure only the test sound generated by the sound generator 8. Therefore, the determination in step S5 of FIG. 5 can be performed with far higher accuracy.

(Modification of Biological Sound Measuring Device 100)

Hereinafter, modifications of the biological sound measuring device 100 will be described.

First Modification

In this modification, it is assumed that a material of the base 11 and the lid 12 of the accommodation case 10 is a material capable of preventing transmission of a sound in a frequency band that each of the first sound measuring instrument M1 and the second sound measuring instrument M2 can measure.

In this configuration, the controller 4 may detect that the accommodation case 10 is attached to the main body 1 based on an intensity of a sound measured by the first sound measuring instrument M1 or the second sound measuring instrument M2.

For example, in step S1 of FIG. 5, the controller 4 may cause the first sound measuring instrument M1 or the second sound measuring instrument M2 to start measuring a sound, and detect that the accommodation case 10 is attached to the main body 1 when an intensity of the sound measured by the first sound measuring instrument M1 or the second sound measuring instrument M2 is equal to or less than a first threshold set in advance.

In the first modification, when the accommodation case 10 is attached to the main body 1, a sound from the outside hardly reaches the first sound measuring instrument M1 and the second sound measuring instrument M2. Therefore, an intensity of the sound measured by each of the first sound measuring instrument M1 and the second sound measuring instrument M2 is greatly reduced as compared with that in a case where the main body 1 is outside the accommodation space SP3 of the accommodation case 10. Accordingly, when the intensity of the sound measured by the first sound measuring instrument M1 or the second sound measuring instrument M2 is equal to or less than the first threshold, it can be determined that the accommodation case 10 is attached to the main body 1.

(Effects of First Modification)

According to the first modification, since the contact sensor 16 can be omitted in the accommodation case 10, it is possible to reduce the cost of the accommodation case 10. Further, when the contact sensor 16 is omitted, terminals of the terminal block 7 of the controller 4 can also be reduced, and reduction in size and cost of the main body 1 and the accommodation case 10 is possible.

Second Modification

In the biological sound measuring device 100, the sound generator 8 is provided in the main body 1. However, the sound generator 8 may be provided in the accommodation case 10. This will be described in detail below.

Figure 6:
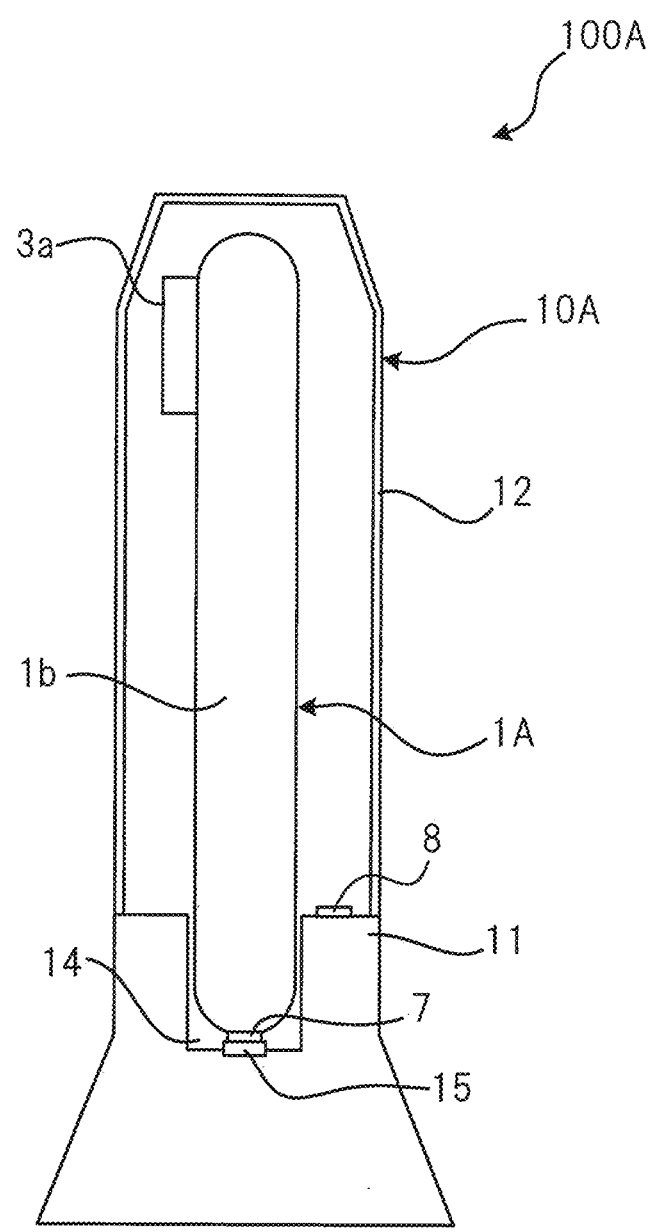
FIG. 6 is a schematic cross-sectional view of a biological sound measuring device 100A as a modification of the biological sound measuring device 100.

FIG. 6 is a schematic cross-sectional view of a biological sound measuring device 100A as a modification of the biological sound measuring device 100. The biological sound measuring device 100A illustrated in FIG. 6 is obtained by changing the main body 1 to a main body 1A and changing the accommodation case 10 to an accommodation case 10A, in the biological sound measuring device 100.

A hardware configuration of the main body 1A is the same as that of the main body 1 except that the sound generator 8 is deleted.

A hardware configuration of the accommodation case 10A is the same as that of the accommodation case 10, except that the sound generator 8 is provided on the base 11 and that the sound generator 8 and the terminal block 15 are connected by a wiring (not illustrated).

The sound generator 8 of the accommodation case 10A is disposed in the accommodation space SP3 between the base 11 and the lid 12 in a state where the lid 12 is attached to the base 11. The sound generator 8 is controlled by the controller 4 of the main body 1A in the same manner as in the biological sound measuring device 100.

(Effects of Biological Sound Measuring Device 100A)

According to the biological sound measuring device 100A, in a state where the main body 1A is accommodated in the accommodation case 10, the sound generator 8 is disposed in the accommodation space SP3 between the base 11 and the lid 12. Therefore, similarly to the biological sound measuring device 100, whether or not the relationship between the measurement sensitivity SM1 and the measurement sensitivity SM2 satisfies the condition can be determined with high accuracy. In addition, since the sound generator 8 is provided on the accommodation case 10A, reduction in size of the main body 1A is possible.

Third Modification

The biological sound measuring device 100 is configured to obtain an environment (a state where the opening 31h is not closed and an ambient sound is insulated) suitable for an inspection mode by using the accommodation case 10 for accommodating the main body 1. However, the environment suitable for the inspection mode can be obtained by using a cover member, instead of the accommodation case 10, which cover a part of the main body 1. This will be described in detail below.

Figure 7:
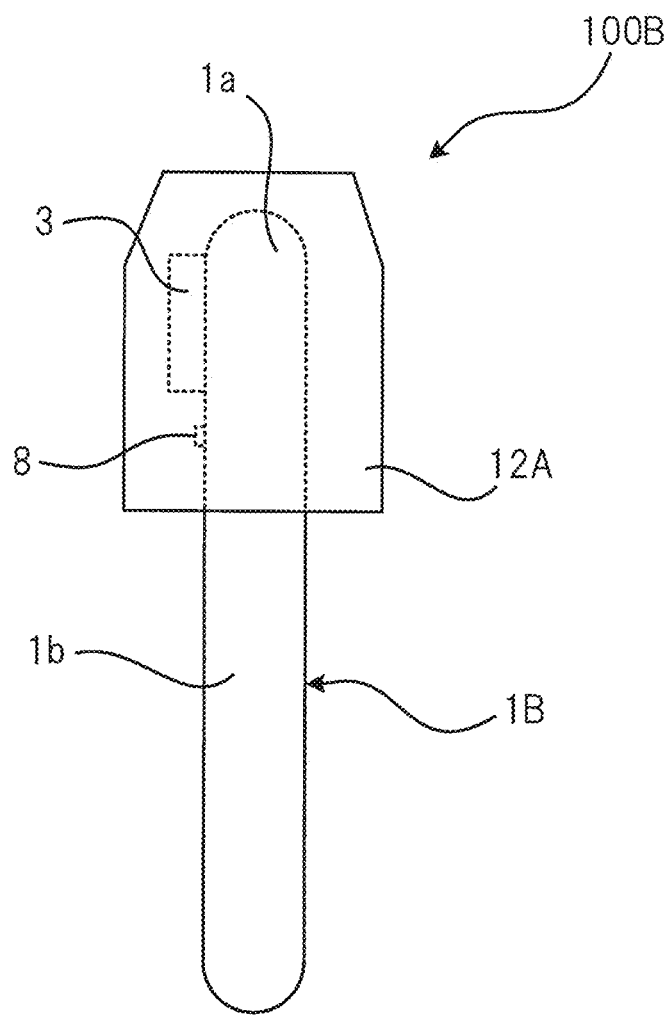
FIG. 7 is a side view of a biological sound measuring device 100B as a modification of the biological sound measuring device 100.

FIG. 7 is a side view of a biological sound measuring device 100B as a modification of the biological sound measuring device 100. The biological sound measuring device 100B illustrated in FIG. 7 includes a main body 1B and a cover member 12A used in the inspection mode. FIG. 7 illustrates a state where the cover member 12A is attached to the main body 1B.

A hardware configuration of the main body 1B is the same as that of the main body 1 except that the terminal block 7 is deleted.

The cover member 12A is a bottomed cylindrical member for covering a portion of the main body 1B where the measuring unit 3 and the sound generator 8 are provided. The main body 1B is inserted into a hollow portion of the cover member 12A from the head portion 1a side, so that the cover member 12A is attached to the main body 1B.

In a state where the cover member 12A is attached to the main body 1B, a gap is formed between an inner wall of the cover member 12A and the pressure receiving portion 3a. That is, in the state where the cover member 12A is attached to the main body 1B, the cover member 12A does not close the opening 31h in the first housing 31 of the main body 1B, and covers the first housing 31, the second sound measuring instrument M2, and the sound generator 8.

Although a material of the cover member 12A is not particularly limited, the material is preferably a material capable of preventing transmission of a sound in a frequency band that each of the first sound measuring instrument M1 and the second sound measuring instrument M2 can measure (reflecting the sound in the frequency band), like the accommodation case 10.

With respect to operations of the biological sound measuring device 100B in the inspection mode, the controller 4 performs processing of determining whether or not the cover member 12A is attached to the main body 1B, in place of the processing of step S1 in the flowchart of FIG. 5. Further, when it is determined that the cover member 12A is attached to the main body 1B, the controller 4 performs the processing of step S2 and subsequent steps.

In the biological sound measuring device 100B, for example, the following methods can be used as a method for the controller 4 to detect that the cover member 12A is attached to the main body 1B.

A first method is a method of providing a contact sensor in the grip portion 1b of the main body 1B, and detecting attachment of the cover member 12A using the contact sensor.

A second method is a method of providing, for example, in the grip portion 1b, an operation button for inputting completion of the attachment of the cover member 12A. In this method, a user of the biological sound measuring device 100B presses the operation button after attaching the cover member 12A to the main body 1B. When the operation button is pressed, an attachment completion signal is input to the controller 4. When receiving the attachment completion signal, the controller 4 detects that the cover member 12A is attached to the main body 1B.

(Effects of Biological Sound Measuring Device 100B)

As described above, according to the biological sound measuring device 100B, effects similar to those of the biological sound measuring device 100 can be obtained. In the biological sound measuring device 100B, the cover member 12A does not cover the entire main body 1B. Therefore, the manufacturing cost of the cover member 12A can be reduced, and the cost of the biological sound measuring device 100B can be reduced.

Fourth Modification

The biological sound measuring device 100 described so far causes the sound generator 8 to generate a test sound in a state where the main body 1 is accommodated in the accommodation case 10, so that a sound, other than the test sound generated by the sound generator 8, is less likely to be measured by the first sound measuring instrument M1 and the second sound measuring instrument M2.

However, when the main body 1 is in a quiet environment, a sound other than the test sound generated by the sound generator 8 is weak, and thus inspection of the measurement sensitivity of the first sound measuring instrument M1 and the second sound measuring instrument M2 can be performed even when the main body 1 is not accommodated in the accommodation case 10. In the fourth modification, a biological sound measuring device 100C that inspects the measurement sensitivity without using the accommodation case 10, as described, will be described.

Figure 8:
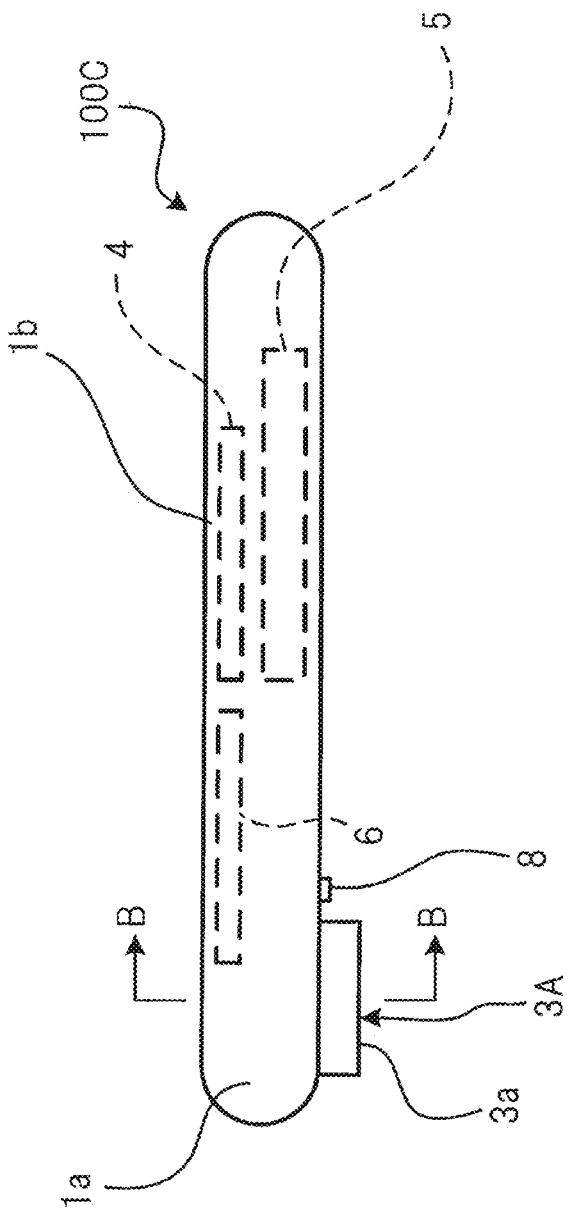
FIG. 8 is a schematic view illustrating a schematic configuration of a biological sound measuring device 100C as a fourth modification of the biological sound measuring device 100.

FIG. 8 is a schematic view illustrating a schematic configuration of the biological sound measuring device 100C as the fourth modification of the biological sound measuring device 100. A hardware configuration of the biological sound measuring device 100C is the same as that of the main body 1 of the biological sound measuring device 100, except that the measuring unit 3 is changed to a measuring unit 3A and that the terminal block 7 is deleted. The biological sound measuring device 100C is an example of a main body of the claims.

Figure 9:
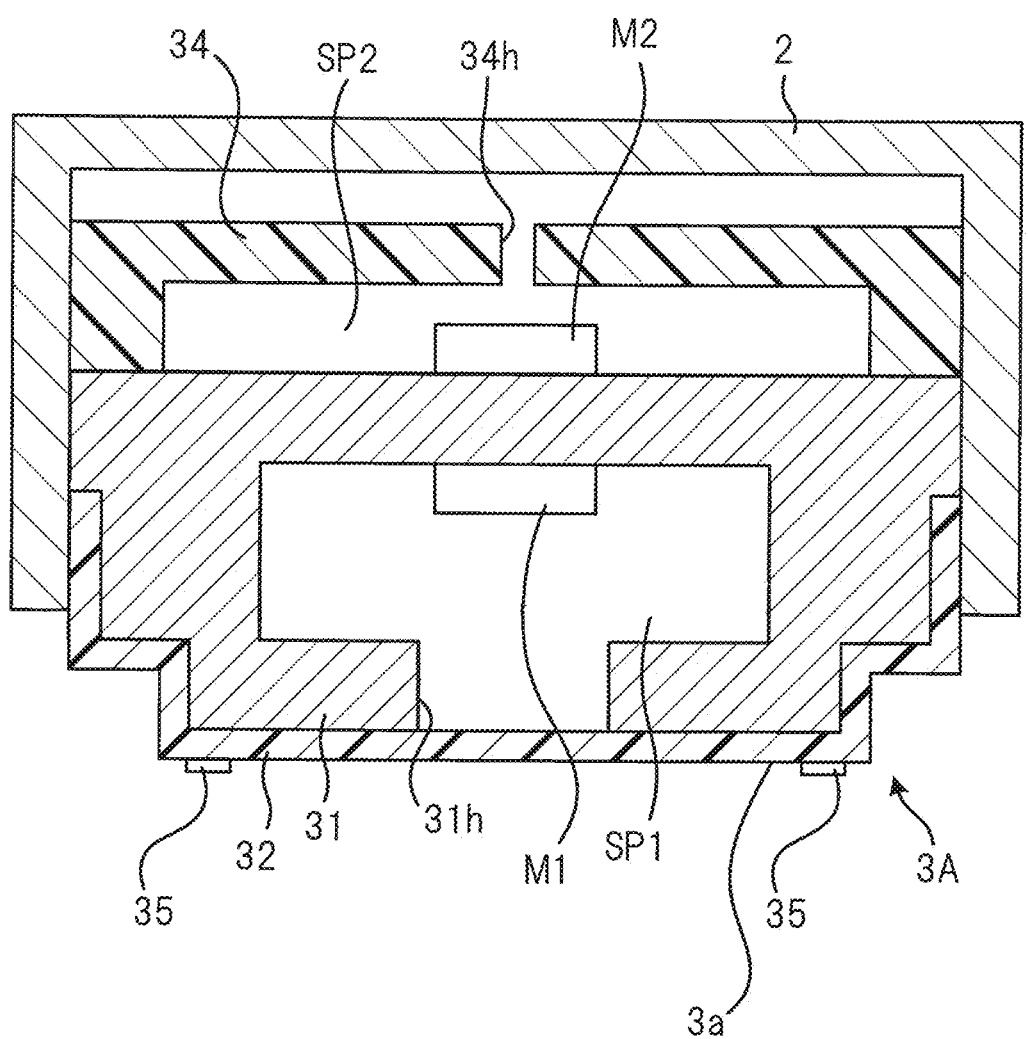
FIG. 9 is a schematic cross-sectional view of the biological sound measuring device 100C taken along a line B-B in FIG. 8.

FIG. 9 is a schematic cross-sectional view of the biological sound measuring device 100C taken along a line B-B in FIG. 8. In FIG. 9, the same components as those in FIG. 2 are denoted by the same reference signs.

The measuring unit 3A of the biological sound measuring device 100C has the same configuration as that of the measuring unit 3 except that a contact sensor 35 is added to a surface of the housing cover 32 which constitutes the pressure receiving portion 3a.

The contact sensor 35 detects contact of an object with respect to the pressure receiving portion 3a. The contact sensor 35 is configured with, for example, a piezoelectric sensor, or a set of a light emitting element that emits light toward the body surface S and a light receiving element that receives reflected light of the light emitted from the light emitting element. When detecting that an object is in contact with the pressure receiving portion 3a, the contact sensor 35 transmits a contact detection signal to the controller 4.

(Operation Example of Biological Sound Measuring Device 100C)

Figure 10:
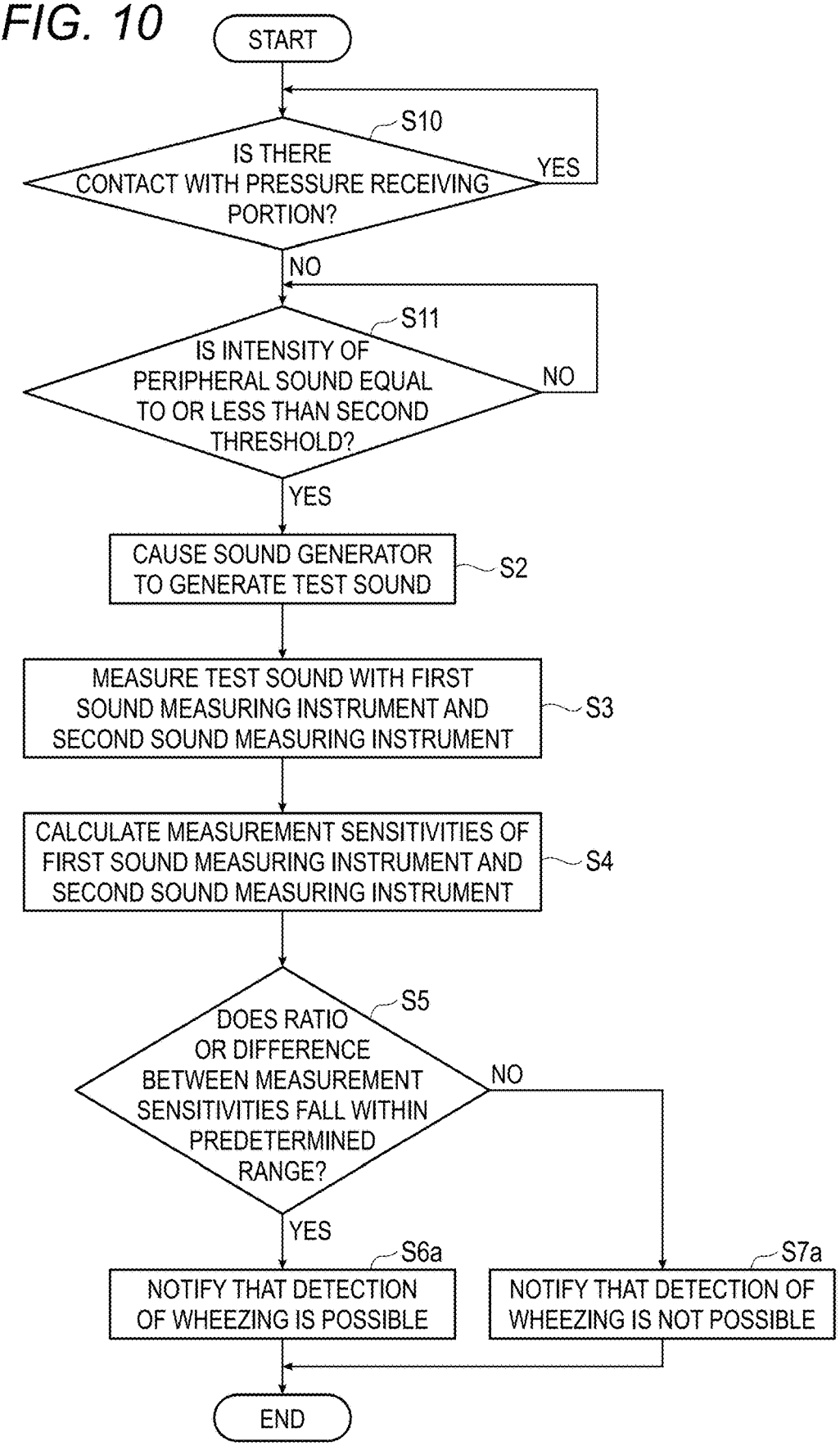
FIG. 10 is a flowchart for illustrating an operation example of the biological sound measuring device 100C illustrated in FIG. 8 in an inspection mode.

FIG. 10 is a flowchart for illustrating an operation example of the biological sound measuring device 100C illustrated in FIG. 8 in an inspection mode. In FIG. 10, the same processing as that illustrated in FIG. 5 is denoted by the same reference sign, and the description thereof will be omitted.

When the inspection mode is set, the controller 4 of the biological sound measuring device 100C determines whether or not an object is in contact with the pressure receiving portion 3a based on an output signal of the contact sensor 35 (step S10).

When an object is in contact with the pressure receiving portion 3a, there is a possibility that the opening 31h of the measuring unit 3A is closed by the object. Therefore, the controller 4 of the biological sound measuring device 100C determines that the opening 31h of the measuring unit 3A is closed when an object is in contact with the pressure receiving portion 3a, and determines that the opening 31h of the measuring unit 3A is not closed when no object is in contact with the pressure receiving portion 3a.

When an object is in contact with the pressure receiving portion 3a (step S10: YES), the controller 4 of the biological sound measuring device 100C performs the determination in step S10 again. When a time period over which an object is in contact with the pressure receiving portion 3a is equal to or longer than a predetermined time period, the controller 4 of the biological sound measuring device 100C may cause the display unit 6 to display a message to prompt for a state to not contact the object with the measuring unit 3A, and notify the user.

When it is determined that no object is in contact with the pressure receiving portion 3a (step S10: NO), the controller 4 of the biological sound measuring device 100C acquires information on a sound measured by the first sound measuring instrument M1 or the second sound measuring instrument M2, and determines whether or not an acquired intensity of the sound is equal to or less than a second threshold set in advance (step S11).

The second threshold is a value for determining whether an environment is suitable for measurement of the test sound generated by the sound generator 8, and a value sufficiently lower than the intensity of the test sound generated by the sound generator 8 is set.

When the determination in step S11 is NO, the controller 4 of the biological sound measuring device 100C performs the processing of step S11 again. When a time period over which the determination in step S11 is NO is equal to or longer than a predetermined time period, the controller 4 of the biological sound measuring device 100C may cause the display unit 6 to display a message for prompting to place the biological sound measuring device 100C in a quiet environment and notify the user.

When the determination in step S11 is YES, the controller 4 of the biological sound measuring device 100C performs the processing of step S2 to step S5.

Further, when the determination in step S5 is YES, the controller 4 of the biological sound measuring device 100C notifies the user that detection of wheezing is possible, by causing the display unit 6 to display that (step S6a).

When the determination in step S5 is NO, the controller 4 of the biological sound measuring device 100C notifies the user that detection of wheezing is not possible, by causing the display unit 6 to display that (step S7a).

A speaker may be mounted in the biological sound measuring device 100C, and in step S7a, the notification may be performed by outputting from the speaker that detection of wheezing is not possible. Alternatively, the biological sound measuring device 100C and an electronic device such as a smartphone may be configured to be able to communicate with each other. A message indicating that detection of wheezing is not possible may be transmitted from the controller 4 to the electronic device, and display or audio output of the message may be performed using a display or a speaker of the electronic device.

Alternatively, for example, an LED may be mounted in place of the display unit 6 of the biological sound measuring device 100C, and when it is determined that the relationship does not satisfy the condition, the controller 4 may notify the user that the measurement accuracy cannot be ensured by causing the LED to emit red light, for example.

(Effects of Biological Sound Measuring Device 100C)

As described above, according to the biological sound measuring device 100C, in the inspection mode, a test sound is generated by the sound generator 8 in a state where the opening 31h in the first housing 31 is not closed. Therefore, the test sound can be measured under substantially the same condition by the first sound measuring instrument M1 and the second sound measuring instrument M2. Accordingly, it is possible to accurately determine whether or not the relationship between the measurement sensitivity of the first sound measuring instrument M1 and the measurement sensitivity of the second sound measuring instrument M2 satisfies the condition.

According to the biological sound measuring device 100C, when a peripheral sound is weak (step S11: YES), a test sound is generated by the sound generator 8. Therefore, decrease of calculation accuracy of the measurement sensitivity due to a peripheral sound of the biological sound measuring device 100C other than the test sound can be prevented, and the determination in step S5 in FIG. 10 can be performed with high accuracy.

According to the biological sound measuring device 100C, the accommodation case 10 and the cover member 12A as described above are not necessary. Therefore, the manufacturing cost of the device can be reduced.

When it is assumed that the inspection mode is set in a state where the biological sound measuring device 100C is in a quiet environment, the processing of step S11 in FIG. 10 is not essential.

Although an embodiment of the present invention and modifications thereof have been described above, the present invention is not limited thereto, and can be modified as appropriate. For example, although the first sound measuring instrument M1 is configured to measure a pulmonary sound as a biological sound in the embodiment and the modifications described above, the first sound measuring instrument M1 may be configured to measure a cardiac sound or the like as a biological sound. In addition, the housing cover 32 of the measuring unit 3 or the measuring unit 3A is not essential and may be omitted.

Although the embodiments are described above with reference to the drawings, it is needless to say that the present invention is not limited to such examples. It will be apparent to those skilled in the art that various changes and modifications may be conceived within the scope of the claims. It is also understood that the various changes and modifications belong to the technical scope of the present invention. Components in the embodiments described above may be combined freely within a range not departing from the spirit of the present invention.

What is claimed is:

1. A biological sound measuring device, comprising:
   a main body including:
   a first sound measuring instrument that is configured to measure a biological sound,
   a housing that accommodates the first sound measuring instrument therein, and that has an opening which is closed by a body surface of a living body in a state where the housing is pressed against the body surface,
   a second sound measuring instrument that is provided outside the housing and that is configured to measure an ambient sound of the housing, and
   a controller that causes a sound generator to generate a sound in a state where the opening in the housing is not closed, that determines whether or not a relationship between a measurement sensitivity of the first sound measuring instrument and a measurement sensitivity of the second sound measuring instrument satisfies a condition set in advance, based on an intensity of the sound measured by the first sound measuring instrument and an intensity of the sound measured by the second sound measuring instrument, and that when it is determined that the relationship does not satisfy the condition, notifies that it is unable to ensure measurement accuracy of biological sound or adjusts the measurement sensitivity of one or both of the first sound measuring instrument and the second sound measuring instrument.

2. The biological sound measuring device according to claim 1, further comprising:
   a cover member that covers the housing and the second sound measuring instrument in the state where the opening in the housing is not closed, and that is detachable with respect to the main body,
   wherein the sound generator is disposed at a position that is covered by the cover member in a state where the cover member is attached to the main body, and
   wherein when attachment of the cover member is detected by the controller, the controller determines that it is the state where the opening in the housing is not closed.

3. The biological sound measuring device according to claim 2,
   wherein the cover member is made of a material that prevents transmission of a sound that the first sound measuring instrument and the second sound measuring instrument can measure.

4. The biological sound measuring device according to claim 3,
   wherein when an intensity of a sound from outside measured by the first sound measuring instrument or the second sound measuring instrument is equal to or less than a first threshold set in advance, the controller detects that the cover member is attached.

5. The biological sound measuring device according to claim 2,
   wherein the sound generator is provided in the cover member.

6. The biological sound measuring device according to claim 2,
   wherein the main body further includes the sound generator.

7. The biological sound measuring device according to claim 1,
   wherein when an intensity of a peripheral sound measured by the first sound measuring instrument or the second sound measuring instrument is equal to or less than a second threshold set in advance and it is the state where the opening in the housing is not closed, the controller causes the sound generator to generate the sound.

8. The biological sound measuring device according to claim 1,
   wherein the main body further includes the sound generator.

9. A method for operating a biological sound measuring device including a first sound measuring instrument that is configured to measure a biological sound, a housing that accommodates the first sound measuring instrument therein and that has an opening which is closed by a body surface of a living body in a state where the housing is pressed against the body surface, and a second sound measuring instrument that is provided outside the housing and that is configured to measure an ambient sound of the housing, the method comprising:
   a step of causing a sound generator to generate a sound in a state where the opening in the housing is not closed, determining whether or not a relationship between a measurement sensitivity of the first sound measuring instrument and a measurement sensitivity of the second sound measuring instrument satisfies a condition set in advance, based on an intensity of the sound measured by the first sound measuring instrument and an intensity of the sound measured by the second sound measuring instrument, and when it is determined that the relationship does not satisfy the condition, notifying that it is unable to ensure measurement accuracy of biological sound or adjusting the measurement sensitivity of one or both of the first sound measuring instrument and the second sound measuring instrument.

10. A storage medium which stores a program for operating a biological sound measuring device including a first sound measuring instrument that is configured to measure a biological sound, a housing that accommodates the first sound measuring instrument therein and that has an opening which is closed by a body surface of a living body in a state where the housing is pressed against the body surface, and a second sound measuring instrument that is provided outside the housing and that is configured to measure an ambient sound of the housing, the program causing a computer to perform a step of:

causing a sound generator to generate a sound in a state where the opening in the housing is not closed, determining whether or not a relationship between a measurement sensitivity of the first sound measuring instrument and a measurement sensitivity of the second sound measuring instrument satisfies a condition set in advance, based on an intensity of the sound measured by the first sound measuring instrument and an intensity of the sound measured by the second sound measuring instrument, and when it is determined that the relationship does not satisfy the condition, notifying that it is unable to ensure measurement accuracy of biological sound or adjusting the measurement sensitivity of one or both of the first sound measuring instrument and the second sound measuring instrument.

* * * * *